(12) United States Patent
Tipirneni

(10) Patent No.: US 9,486,265 B2
(45) Date of Patent: Nov. 8, 2016

(54) ORTHOPEDIC BONDING AGENT APPLICATION TOOL

(71) Applicant: Tipirneni Software LLC, Glendale, AZ (US)

(72) Inventor: Kishore Tipirneni, Glendale, AZ (US)

(73) Assignee: TIPIRNENI SOFTWARE LLC, Glendale, AZ (US)

(*) Notice: Subject to any disclaimer, the term of this patent is extended or adjusted under 35 U.S.C. 154(b) by 0 days.

(21) Appl. No.: 14/996,509

(22) Filed: Jan. 15, 2016

(65) Prior Publication Data

US 2016/0128753 A1  May 12, 2016

Related U.S. Application Data

(63) Continuation of application No. 13/676,977, filed on Nov. 14, 2012, now Pat. No. 9,265,547.

(51) Int. Cl.
*A61B 17/58* (2006.01)
*A61B 17/88* (2006.01)
*A61B 17/00* (2006.01)
*A61F 2/46* (2006.01)

(52) U.S. Cl.
CPC ..... *A61B 17/8827* (2013.01); *A61B 17/00491* (2013.01); *A61B 17/8805* (2013.01); *A61F 2/46* (2013.01); *A61F 2002/4631* (2013.01)

(58) Field of Classification Search
CPC .............. A61B 17/16; A61B 17/1604; A61B 17/8805; A61B 17/00491; A61B 2017/1602; A61B 2/4601; A61F 2002/2835
USPC .................. 433/37, 45–48, 71, 214; 606/93; 15/236.05–236.06, 236.08–236.09, 15/141.1, 142
See application file for complete search history.

(56) References Cited

U.S. PATENT DOCUMENTS

| | | | | |
|---|---|---|---|---|
| 441,244 | A * | 11/1890 | Kavel | A22C 25/025 15/236.06 |
| 3,140,500 | A * | 7/1964 | Pilla | E04F 21/06 15/235.4 |
| 4,375,965 | A * | 3/1983 | Weissman | A61C 9/0006 433/37 |
| 6,280,472 | B1 | 8/2001 | Boucher et al. | |
| 7,115,172 | B1 * | 10/2006 | Teodorovich | E04F 21/16 134/42 |
| 2003/0055507 | A1 | 3/2003 | McDevitt et al. | |
| 2007/0288032 | A1 * | 12/2007 | Metzger | A61B 17/025 606/99 |
| 2009/0105772 | A1 | 4/2009 | Seebeck et al. | |

OTHER PUBLICATIONS

Web Page : Jim Moore Glass Tools, Hand Stamps, Honeycomb Fine Texture Pad (35.00), Dated Aug. 2009 http://toolsforglass.com/store/crimps.html.*
Office Action dated May 22, 2015 in U.S. Appl. No. 13/676,977.
(Continued)

*Primary Examiner* — Anu Ramana
*Assistant Examiner* — Jessica Weiss
(74) *Attorney, Agent, or Firm* — Snell & Wilmer L.L.P.

(57) ABSTRACT

The present disclosure relates to a tool for injecting a bonding agent into the prepared end of a bone for bonding a joint replacement device to the bone. The tool incorporates vented cells for containing the bonding agent. Force is applied to the back of the tool, while placing the front of the tool filled with bonding agent against the prepared bone area. The force causes the cells to cut into the end of the prepared bone. The force also causes the bonding agent to be forced deep into the cuts and pores of the bone.

19 Claims, 14 Drawing Sheets

(56) References Cited

OTHER PUBLICATIONS

Final Office Action dated Dec. 1, 2015 in U.S Appl. No. 13/676,977.
Notice of Allowance dated Jan. 11, 2016 in U.S Appl. No. 13/676,977.

Web Page: Jim Moore Glass Tools, Hand Stamps, Honeycomb Fine Texture Pad (35.00), 7 pages, Dated Aug. 2009, http://toolsforglass.com/store/crimps.html.

* cited by examiner

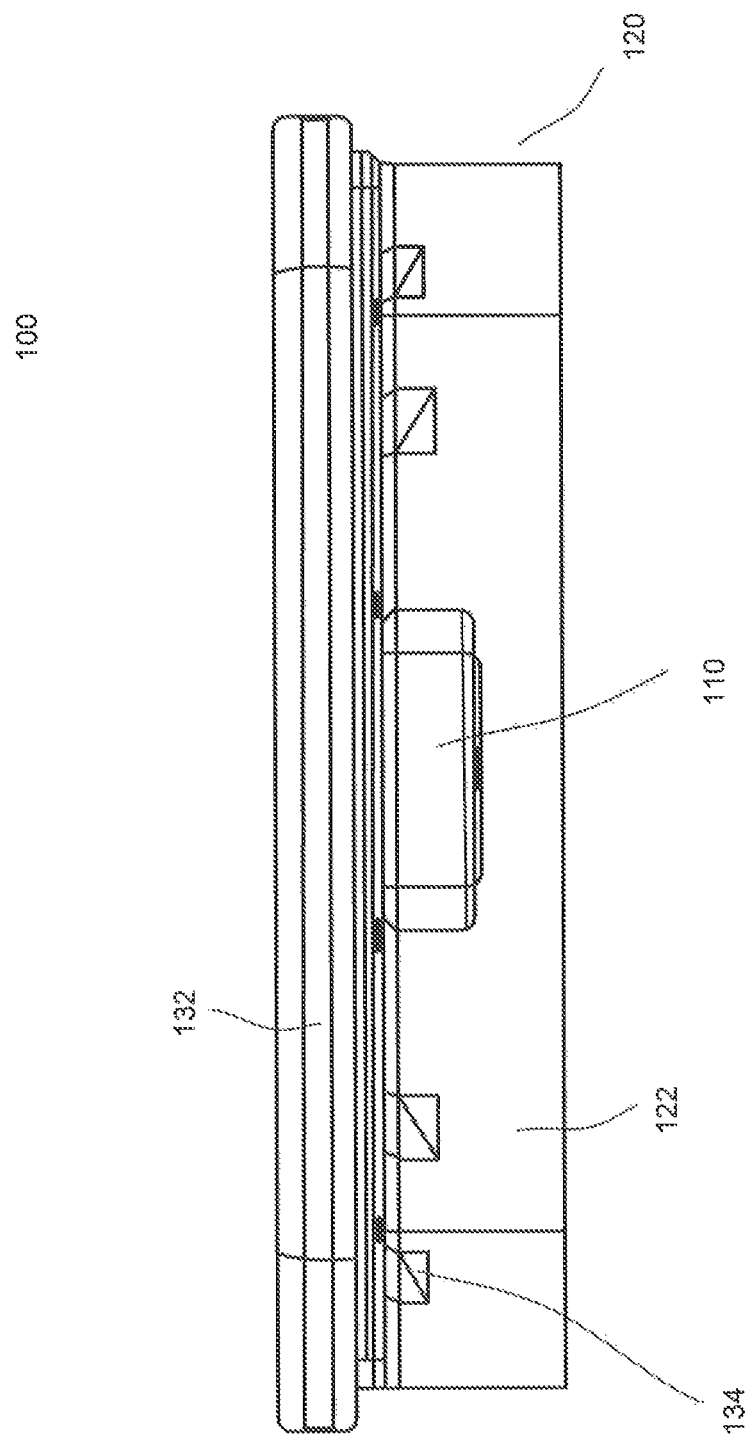

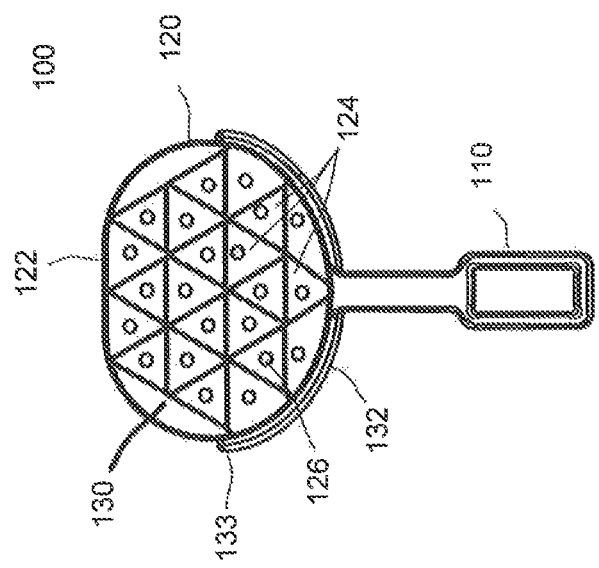
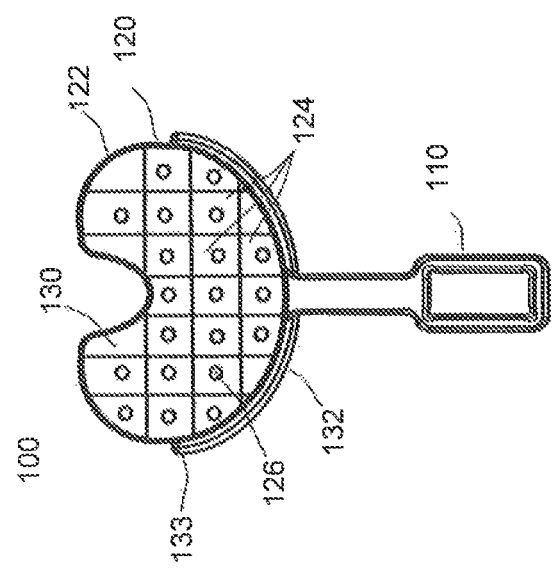

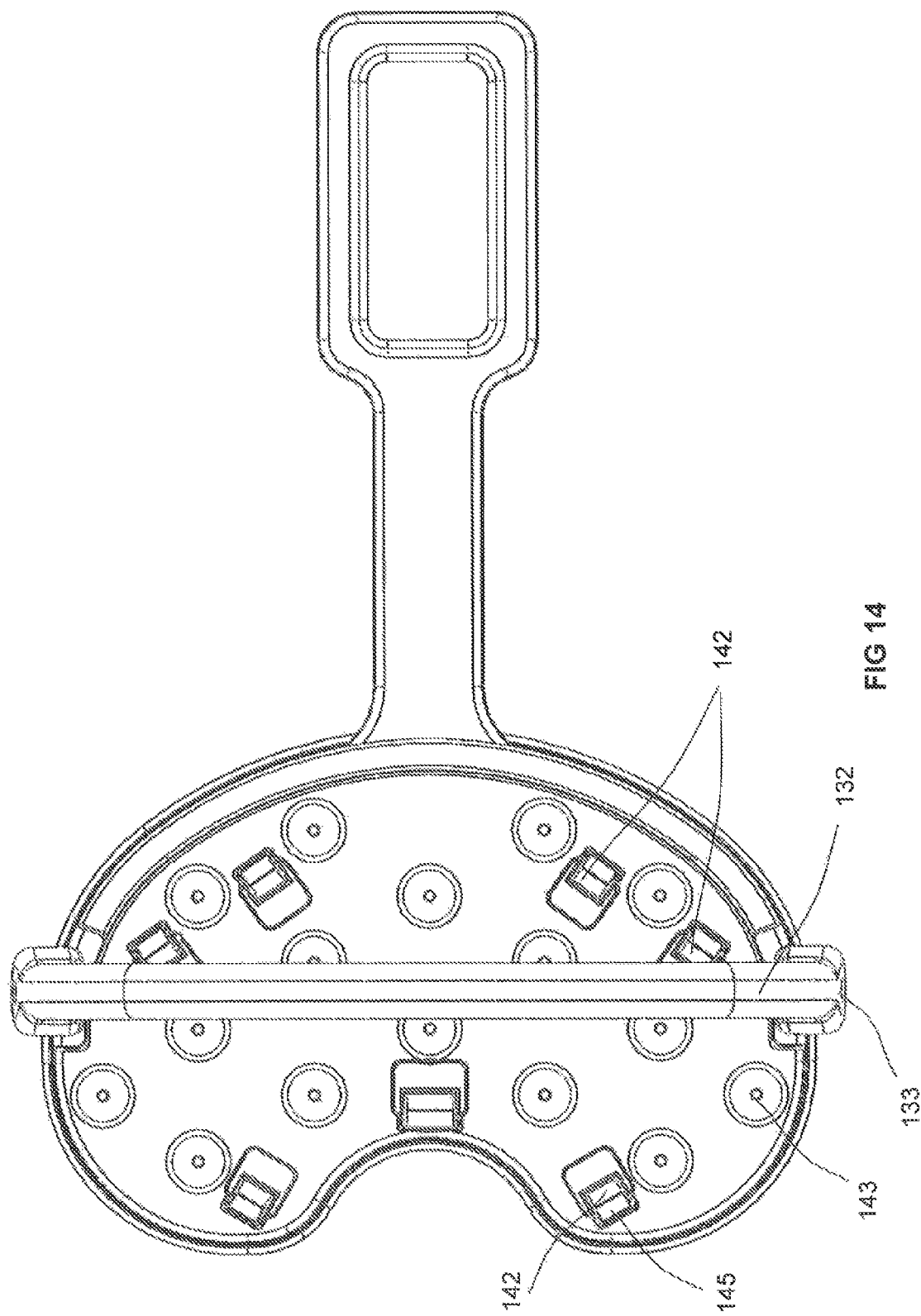

ORTHOPEDIC BONDING AGENT APPLICATION TOOL

CROSS REFERENCE TO RELATED APPLICATIONS

This application is a continuation of, claims priority to and the benefit of, U.S. Ser. No. 13/676,977 filed on Nov. 14, 2012 and entitled "ORTHOPEDIC BONDING AGENT APPLICATION TOOL," which is incorporated by reference herein in its entirety.

FIELD OF DISCLOSURE

The present disclosure relates generally to a tool for aiding in the injection of bonding agent into the knee during knee replacements.

BACKGROUND OF THE DISCLOSURE

Joint replacement surgery is usually performed on patients that have damage to the surface of the bones that make up the joint. For example, in knee replacement surgery, a femoral and/or a tibial replacement joint provides a new surface contact in the joint. During application of the replacement surfaces, a bonding agent (e.g., polymethylmethacrylate cement) is used to attach the replacement joint to the bone. A major shortcoming of the joint replacement surgery is that the bond between the replacement joint and the bone tends to breakdown quicker than the replacement joint. This premature breakdown of the bond unnecessarily limits the life of the replacement joint.

SUMMARY OF THE DISCLOSURE

In accordance with various embodiments, the present disclosure includes a tool for an improved orthopedic joint replacement procedure, wherein the tool aids in the injection of the bonding agent. An apparatus for aiding in an orthopedic joint replacement may comprise a handle portion for gripping a head portion that may contain a bonding agent. The head portion may further comprise a base plate, an external wall and a plurality of cells within the external wall defined by internal walls. The handle may be attached at one end to one of at least the exterior side of the external wall or the baseplate. At least one or more of the plurality of cells may include a through hole at the bottom of the cell. A portion of the plurality of cells may be similarly shaped. A portion of the plurality of cells may be dissimilarly shaped. The similarly shaped cells may be honeycomb shaped. The dissimilarly shaped cells may connect the honeycomb shaped cells to the external side wall. The head may conform to the shape of the bone (e.g., end of the bone) for which the head is applied. The head may be shaped similar to the distal end of the femur. The head may be shaped similar to the proximal end of the tibia. The head may be a "bean" shape (e.g., oblong with a convex side and a concave side, and rounded on the ends) and slightly larger than the distal end of the femur. The side wall of the baseplate may further comprise a rib wrapping around at least half of the tool on the side nearest to the handle. The external wall may also further comprise holes. While described herein with the end of the bone, the tool may be applied to any surface of the bone.

In accordance with various embodiments, the present disclosure includes a method for applying a bonding agent to a bone that is prepared to receive the bonding agent as part of a joint replacement procedure. The method may include obtaining a bonding agent application tool comprising a handle and a head. The head may comprise a base plate and a plurality of cells. The cells may be filled with the bonding agent. The top of the walls of the plurality of cells may be placed against the prepared bone end where the joint is being replaced. A force may be applied to the base plate forcing the cells to cut into the bone and forcing the bonding agent into the cuts and pores in the bone. The force may be applied to the baseplate by striking the baseplate with a mallet. The tool may be removed from the end of the bone. The replacement joint may be oriented in the area prepared with the bonding agent. The method may be repeated for the second bone in the joint. The first bone may be the distal end of the femur and the second bone may be the proximal end of the tibia.

BRIEF DESCRIPTION OF THE DRAWINGS

The drawings described herein are for illustration purposes only and are not intended to limit the scope of the present disclosure in any way. The present disclosure will become more fully understood from the detailed description and the accompanying drawings wherein:

FIG. 6 is a bottom view of a bonding agent application tool, in accordance with various embodiments;

FIG. 7a is a front view of a bonding agent application tool with square cells, in accordance with various embodiments;

FIG. 7b is a front view of a bonding agent application tool with triangular cells and an oval shaped head, in accordance with various embodiments;

FIG. 14 is a front view of a bonding agent application tool with an extended handle, in accordance with various embodiments.

DETAILED DESCRIPTION

Figure 1:
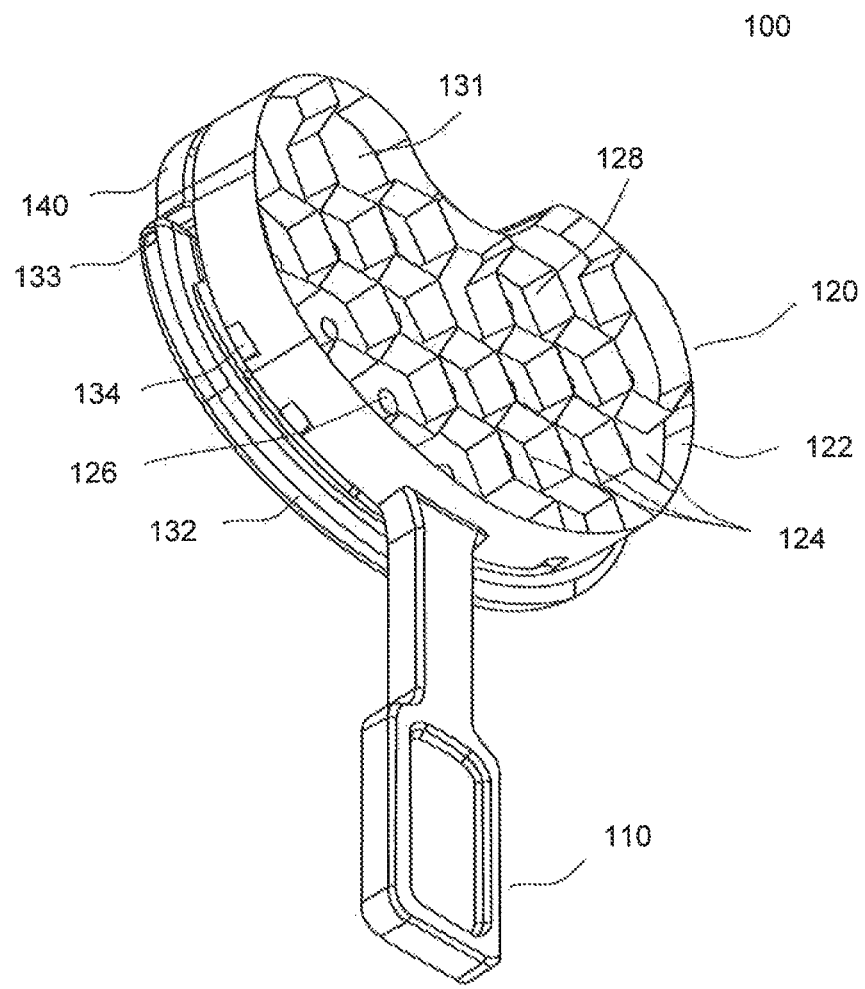
FIG. 1 is an isometric front view of a bonding agent application tool, in accordance with various embodiments.

The detailed description of exemplary embodiments herein makes reference to the accompanying drawings, which show exemplary embodiments by way of illustration and its best mode. While these exemplary embodiments are described in sufficient detail to enable those skilled in the art to practice the invention, it should be understood that other embodiments may be realized and that logical, chemical and mechanical changes may be made without departing from the spirit and scope of the invention. Thus, the detailed description herein is presented for purposes of illustration only and not of limitation. For example, the steps recited in any of the method or process descriptions may be executed in any order and are not necessarily limited to the order presented. Moreover, many of the functions or steps may be outsourced to or performed by one or more third parties. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

The present disclosure relates to a tool for improving joint replacement surgery. During joint replacement surgery, a bonding agent is applied to the end of a bone that is intended to receive the new joint surface. In accordance with various embodiments, a tool is configured to inject a bonding agent into the end of a bone that has been prepared for surgery. In various embodiments, the tool may be configured to prevent (or minimize) the bonding agent from flowing laterally out of the tool. The tool may be configured to force the bonding agent to flow into the bone. The tool may be configured to apply the bonding agent in a uniform depth. The tool may be configured to apply varying amounts of pressure to the bonding agent when injecting the bonding agent into the bone. The tool may be configured to apply a different amount of pressure to the bonding agent depending on the area of the bone the bonding agent is being applied. The tool applies the bonding agent by cutting into the bone and forcing the bonding agent against the bone and the cuts. In various embodiments, the tool applies the bonding agent, cuts into the bone and forces the bonding agent against the bone and the cuts, all during the same process. The tool incorporates vented cells for containing the bonding agent. Force is applied to the back of the tool, while placing the front of the tool filled with bonding agent against the prepared bone area. The force causes the cells to cut into the end of the prepared bone. The force also causes the tool to force the bonding agent into (e.g., deeper into) the cuts and pores of the bone. By applying the bonding agent deep into the surface of the bone, the bonding agent may obtain a stronger hold on the replacement joint and be less exposed to the various conditions inside of the patient. To achieve good depth (e.g., greater than 5 mm), the orthopedic bonding agent application tool may include features that aid in penetrating the bonding agent into the bone.

In accordance with various embodiments, and as illustrated in FIGS. 1-7, the tool may be a handheld device used in surgery. For example, the tool may comprise a handle 110 configured as a gripping surface and may be configured to be comfortable and/or ergonomic. Handle 110 may be long and narrow, suitable for holding in the palm of the hand. Handle 110 may further be sufficiently strong and rigid to withstand or resist high forces applied to the tool during surgery. Handle 110 may be configured to be held in one hand by a surgeon, thereby enabling the free hand to provide the force desired to apply the bonding agent.

In accordance with various embodiments, and as illustrated in FIGS. 1-7, the tool may be configured to receive and contain a bonding agent. For example, the tool may comprise a head 120 configured to contain the bonding agent. Head 120 may also be configured to apply the bonding agent to the bone. Head 120 may be configured to cut into the bone. Head 120 may be configured to receive an application of force for both driving the bonding agent into the bone, as well as cutting into the bone itself.

In accordance with various embodiments, and as illustrated in FIGS. 1-8, head 120 may be attached to handle 110. Head 120 may have an external wall 122 which defines the exterior shape of head 120. Furthermore the external wall 122 may also define a container area for holding the bonding agent. Head 120 may have any shape sufficient to deliver the bonding agent to the bone. In accordance with various embodiments, head 120 may comprise the shape of the end of the bone for which the head is applied. In one example, head 120 may be shaped similar to the distal end of the femur. In another example, head 120 may be shaped similar to the proximal end of the tibia. In another example, head 120 may be shaped like a bean (round on the ends with a concave side and a convex side). In another example, head 120 may be any shape provided it is suitable to deliver the bonding agent without damaging the surrounding tissue (see, e.g., FIG. 7b for alternative oval shape).

Figure 2:
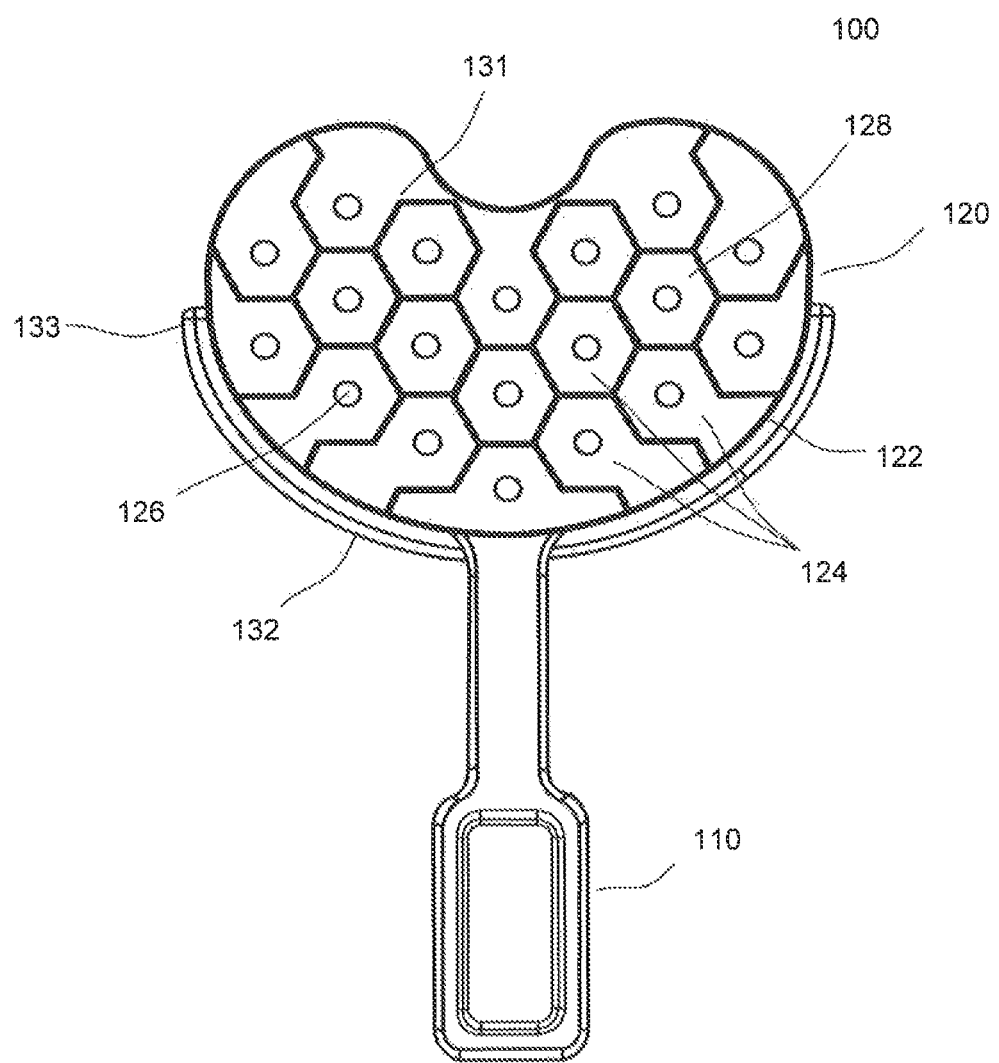
FIG. 2 is an back view of a bonding agent application tool, in accordance with various embodiments.

In accordance with various embodiments, as illustrated in FIGS. 1-3, 5-7, and 9-13 head 120 may further comprise a top plate 130 which mates with a baseplate 140. The top plate may comprise the external wall 122. As discussed herein, external wall 122 may provide a vertical boundary (i.e., a wall perpendicular to the broad surface area of the tool, for example FIG. 2 illustrates an exemplary embodiment of the broad surface area of the tool) around the periphery of head 120 creating the container portion of head 120. Top plate 130 may comprise cells 124. Cells 124 may comprise additional perpendicular walls further subdividing the area within external wall 122. Top plate 130 may comprise a bottom surface 131 which operates as a lower barrier. Top plate 130 may comprise hole 126 through bottom surface 131. The cells 124 and external wall 122 may extend from a first side of top plate 130. Top plate 130 may include pegs 142 which extend from a second side of top plate 130. Pegs 142 may be located on top plate 130 on a side which mates with baseplate 140. Pegs 142 may engage baseplate 140 attaching the two items. In various examples, peg 142 may be attached to the top plate at one end. As illustrated in figure for example, peg 142 may have a protrusion 145 at the second end. Peg 142 may be sufficiently flexible to deform in response to be inserted into hole 144. Once inserted into hole 144, peg 142 may return to its previous position and cause protrusion 145 to hook over retain the surface of base plate 140.

Figure 10:
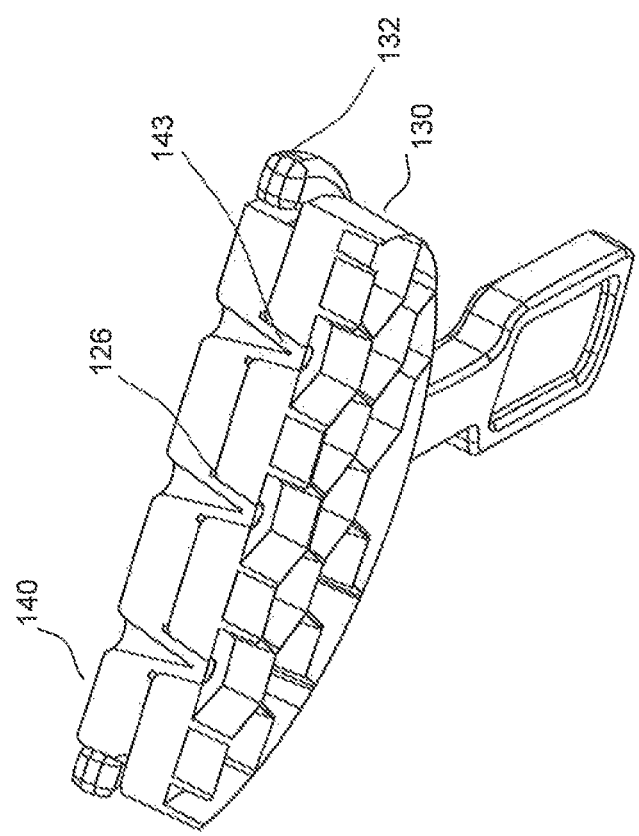
FIG. 10 is an isometric cross sectional view of a bonding agent application tool illustrating a cross section of the engagement between a plurality of holes in a top plate and a plurality of plugs in a baseplate, in accordance with various embodiments.

In accordance with various embodiments, and as illustrated in FIGS. 1 and 3-5, head 120 may further comprise a baseplate 140 which may be moveably attached to the top plate 130. Baseplate 140 may be configured to be sufficiently strong to receive sufficient force to drive the head of the tool and the bonding agent into the bone without breaking. For example, the baseplate may be configured to receive any force such as a mallet strike. As illustrated in FIG. 10, baseplate 140 may comprise plugs 143. Plugs 143 may be configured to pass through and/or seal holes 126. Baseplate 140 may comprise holes 144. Holes 144 may be located and configured to receive pegs 142.

Figure 3:
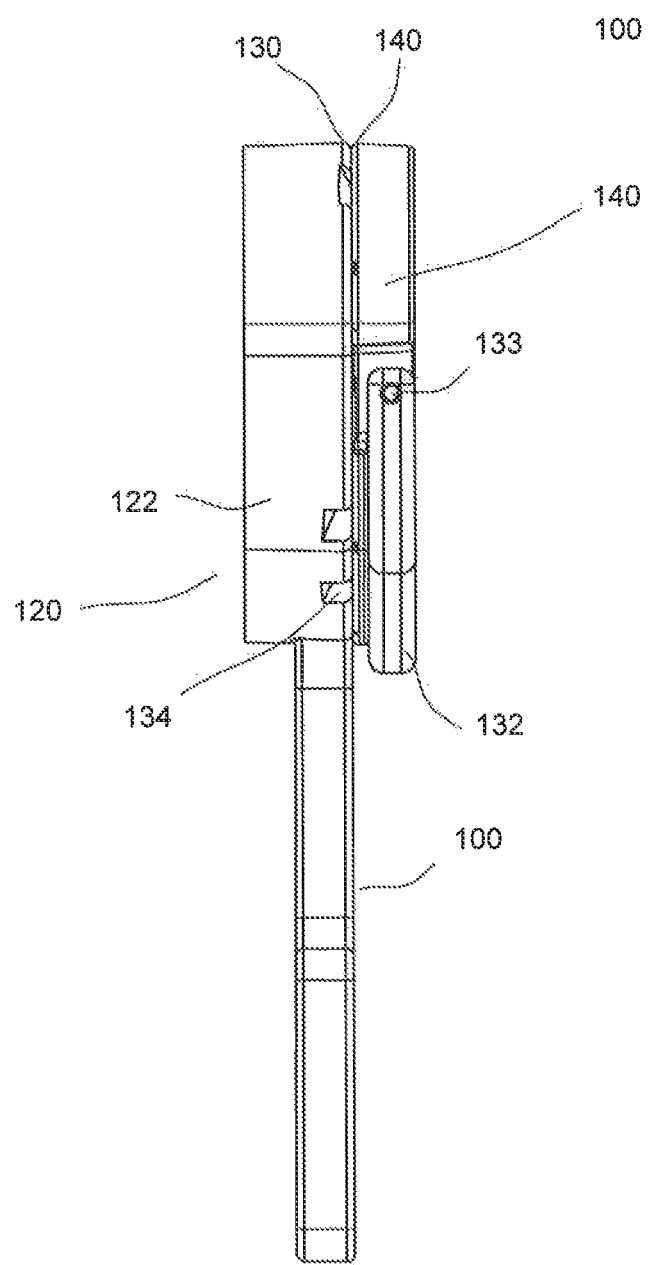
FIG. 3 is a side view of a bonding agent application tool, in accordance with various embodiments.
Figure 4:
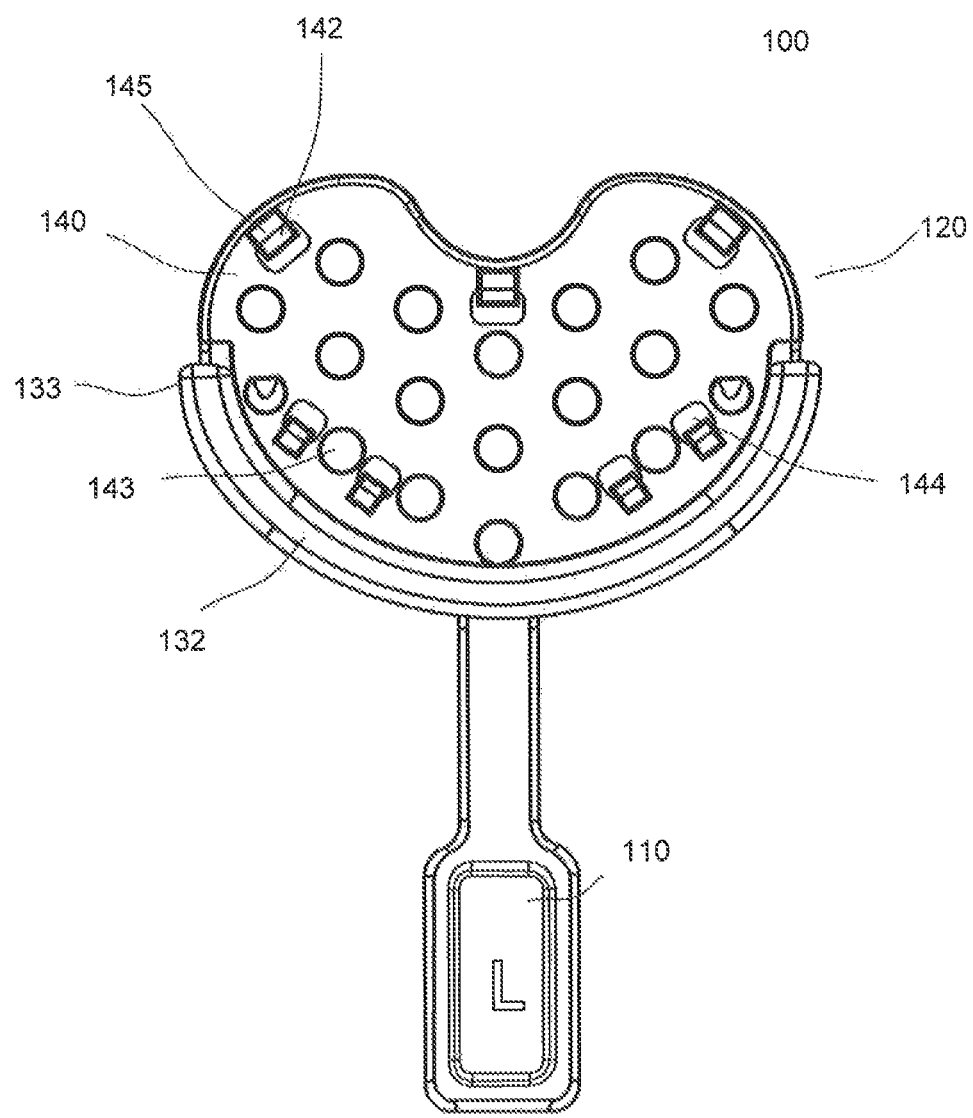
FIG. 4 is a front view of a bonding agent application tool, in accordance with various embodiments.
Figure 5:
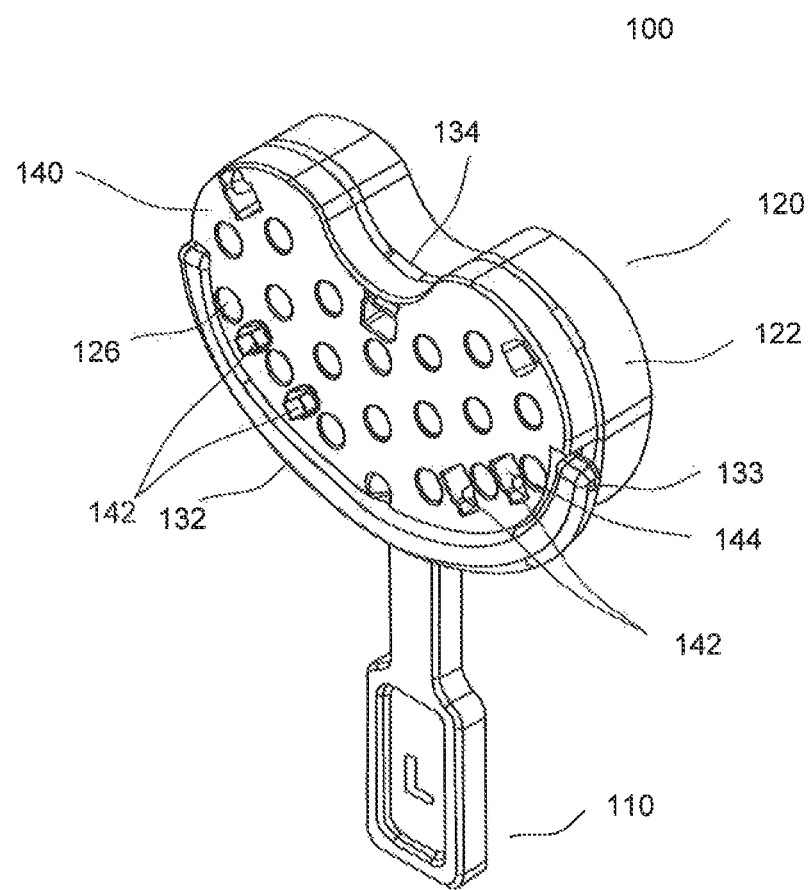
FIG. 5 is an isometric back view of a bonding agent application tool, in accordance with various embodiments.
Figure 11:
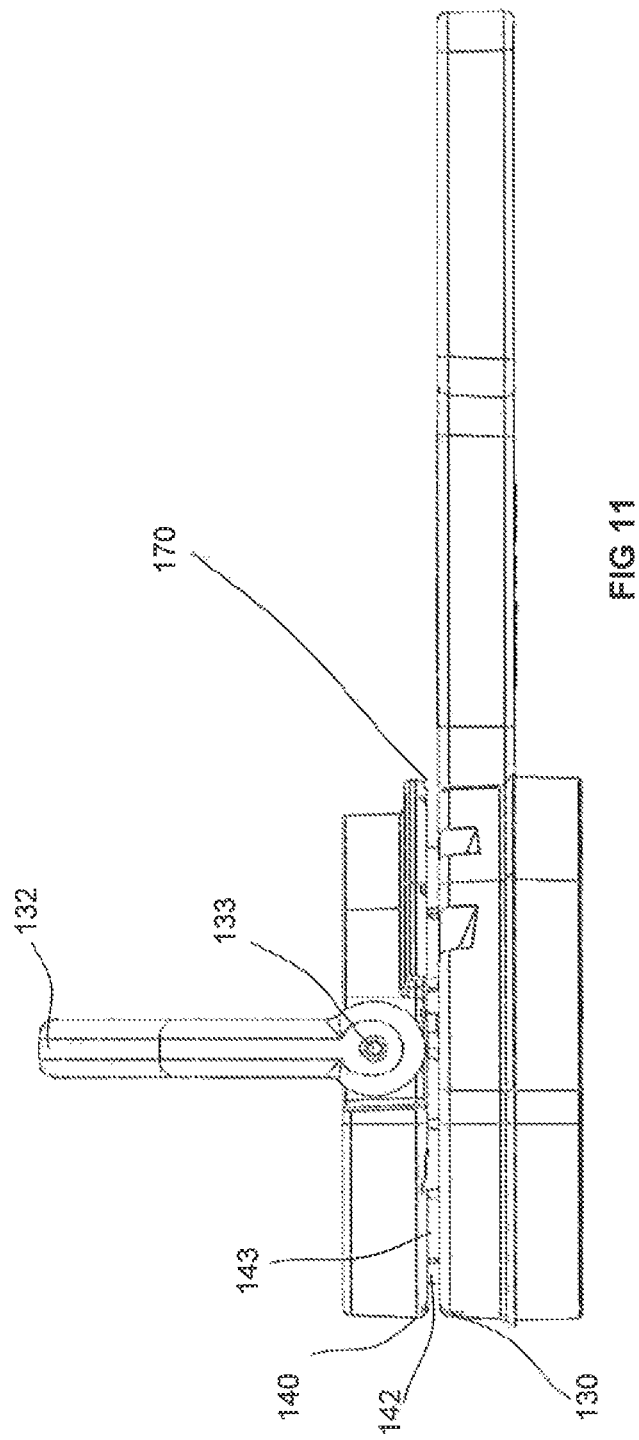
FIG. 11 is a side view of a bonding agent application tool with an extended handle, in accordance with various embodiments.
Figure 12:
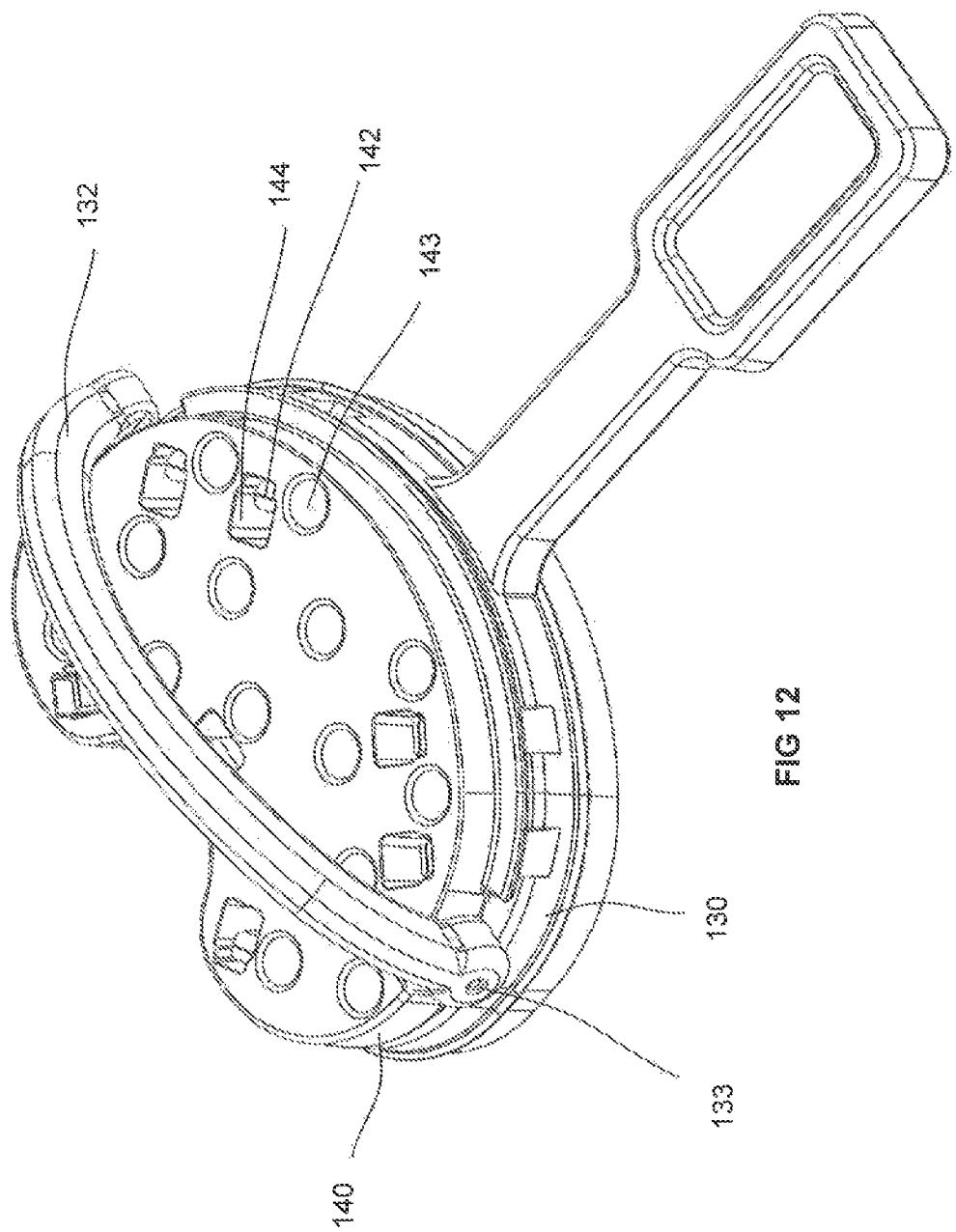
FIG. 12 is an isometric view of a bonding agent application tool with an extended handle, in accordance with various embodiments.
Figure 13:
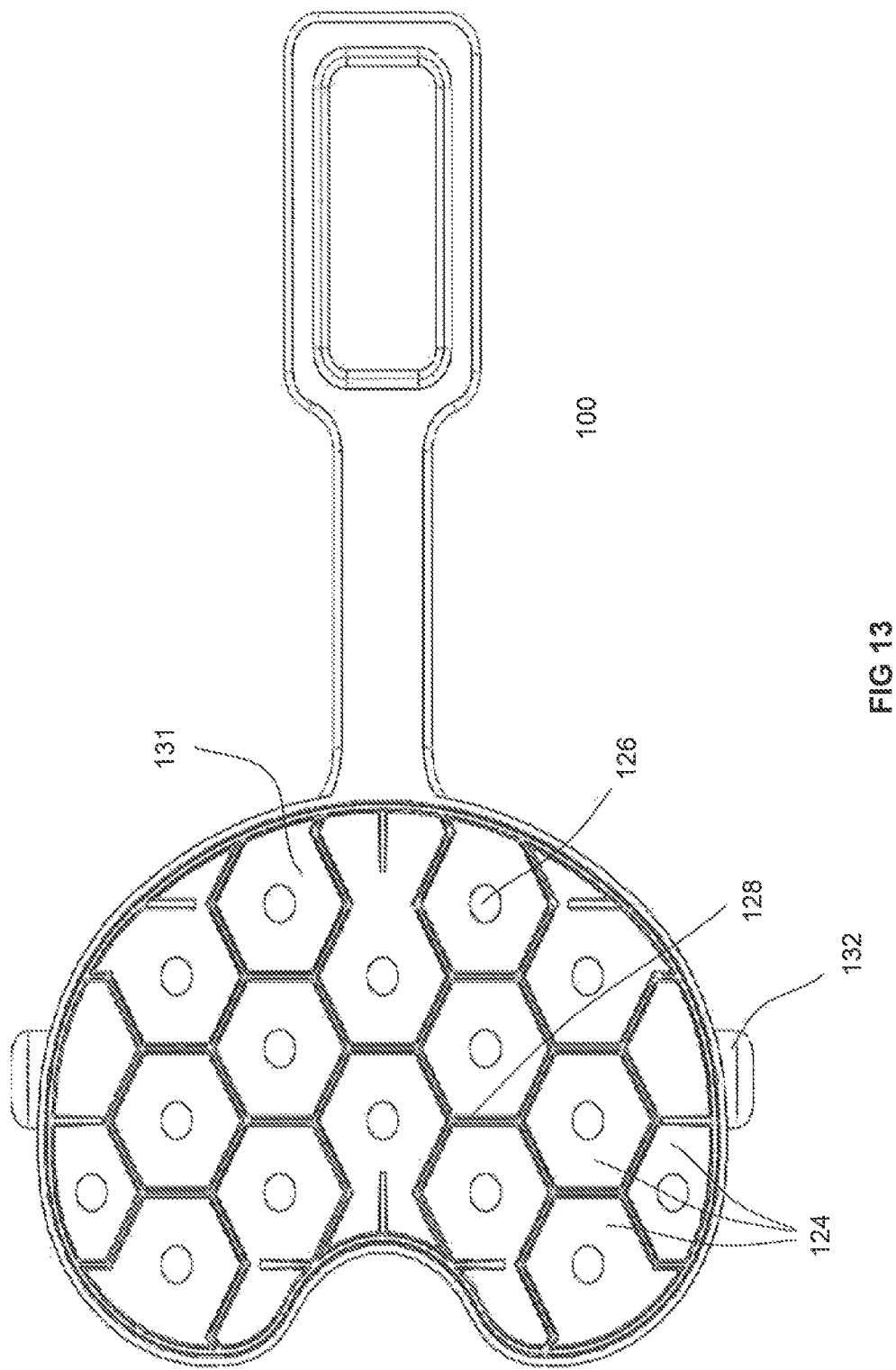
FIG. 13 is an back view of a bonding agent application tool, in accordance with various embodiments.

In accordance with various embodiments, and as illustrated in FIGS. 1-6, 11-12, and 14, head 120 may further comprise an extraction handle 132. Extraction handle 132 may extend around the periphery of the head. In one example, the extraction handle may be connected to baseplate 140 of head 120 by a pivot point 133 on each end of the handle. In another example, the extraction handle may be connected to the external wall 122 of head by a pivot point 133 on each end of the handle. As illustrated in FIGS. 11 and 12 for example, Pivot point 133 may allow the extraction handle to rotate up and away from the plurality of cells 124 until it is perpendicular to base plate 140. Also, as illustrated in FIGS. 3-5 for example, the pivot point 133 may allow the extraction handle to lay parallel to the baseplate such that the baseplate can be struck with a mallet without being interfered with by extraction handle 132. Extraction handle 132 may be configured to apply a force away from the tool and bone, such that when the tool has been used to apply the bonding agent on the bone, the handle may pull at least one of the tool, the baseplate, and the top plate away from the bone.

In accordance with various embodiments, as illustrated in FIGS. 1, 3, 5-6, and 10-14, base plate 140 may be connected to an extraction handle 132. By applying a force on the handle, while top plate 130 is restrained (for example restrained by forces caused by the bone and adhesive after application of the adhesive into the bone), the top plate separates slightly from the baseplate, but still remains attached to the base plate. This separation unseals the holes 126 to allow air in the cells 124. In such an example holes 126 may operate as vent holes. The tool may then be removed from the bone, leaving the injected bonding agent substantially intact within in the bone and not within the tool. In various examples, plug 143 may be configured to substantially seal the holes 126 when the bonding agent is being injected and when the base plate and the top plate separate plug 143 may unseat from holes 126.

In various embodiments, the top plate may be separated from the baseplate. For example the base plate and the top plate may be separated manually, after the bonding agent has been injected. The top plate may be connected to the baseplate in any manner known in the art. For example, a latch or screw may connect the top plate and the baseplate. In another example. The base plate may attach to the top plate by pegs 142 which pass through holes 144. In response to passing through holes 144 pegs 142 may secure the base plate to the top plate, allowing the two to separate only a small distance. See for example the gap 170 between top plate 130 and baseplate 140 illustrated in FIG. 11.

In accordance with various embodiments, as illustrated in FIGS. 1-2, 7, and 13, head 120 may comprise a plurality of cells 124. The plurality of cells 124 may be configured to hold a small amount of bonding compound in each of the plurality of cells. The plurality of cells may also comprise a thin wall surrounding a discrete area within the external wall. The thin wall section may be sufficiently thin and sufficiently strong to cut into the bone in response to sufficient force. Each cell 124 may have a vertical wall parallel with the external wall. Each cell 124 may be a subdivision of the entire area defined by external wall 122. In accordance with various embodiments, the cells may comprise any shape suitable to contain bonding compound, cut into bone, and/or apply bonding compound. In one example, each cell 124 is a square (e.g., FIG. 7*a*). In another example, each cell 124 is triangular (e.g., FIG. 7*b*). In another example, each cell 124 is a honeycomb shape as depicted by cell 128 (e.g., FIG. 2). In another example, only a portion of the cells are similar to one another in size and shape, (e.g., honeycomb cells 128 in FIG. 2). The remaining cells may be configured in size and shape configured to attach the similar shaped cells to external wall 122 (e.g., cell 130 of FIG. 2 are irregular shaped).

In accordance with various embodiments, the compartmentalized cells 124 are configured such that the cells prevent or minimize the bonding agent from flowing laterally. The cells are configured to allow the bonding agent to flow into the bone. Without being bound by theory it is believed that the bone, due to its varying density, requires different pressures (sometimes very different pressures) to the bonding agent in order get similar depth of penetration of the bonding agent. This relatively uniform depth of penetration improves implant longevity. For example, the edges of the bone require much higher pressure for penetration when compared to the central area of the bone. Without compartmentalized cells, any pressure on the bonding agent would cause it to mainly flow to the path of least resistance. If the path of least resistance is laterally out of the joint and/or into less dense bone, then penetration would not be uniform. For example, the bonding agent may flow toward the center of the bone (a less dense region) resulting in much more depth of penetration at the center of the bone, with little penetration towards the edge of the bone where there is a greater need for penetration. Compartmentalized cells 124 may prevent or minimize such flow. Cells 124 are configured to substantially maintain the bonding agent in each compartment. Cells 124 may allow for substantially even penetration of the bonding agent, regardless of the amount of pressure needed. In response to striking the baseplate with a mallet, this cellular structure automatically may allow for increased pressure where the bone is denser and decreased pressure where the bone is less dense.

In accordance with various embodiments, and as illustrated in FIGS. 1-2, 4-5, 7, and 9-10, head 120 may comprise a plurality of through holes 126 which pass through top plate 130. Each of these through holes may be located in any position on the baseplate. One or more cells may contain through holes 126 through the baseplate. For example, through holes 126 may be centered within all of cells 124. Through holes 126 may be configured as a vent. Once the head of the tool is seated into the bone and the bonding agent is applied vent holes 126 may be opened allowing the head of the tool to be removed more easily. In various examples, through holes 126 in the baseplate may allow for air to enter into the cells to prevent or minimize a vacuum and allow the injected bonding agent to substantially remain in the bone when removing the tool from the bone. For example, plug 143 may plug hole 126. In response to pulling on extraction handle 132 while removing the tool from the bone. Handle 132 may cause base plate 140 to separate from top plate 130. This separation may cause plug 143 which may be attached to base plate 140 to separate from top plate 130.

In accordance with various embodiments, tool 100 may be manufactured in one part or in multiple parts. For example, tool 100 may be a single cast part. In another example, tool 100 may comprise one or more parts including a separate base plate, top plate, external wall and cell portion, extraction handle, and/or handle. The base plate may attach to the top plate by using pegs 142 which pass through holes 144. In response to passing through holes 144 pegs 142 may secure the base plate to the top plate, allowing the two to separate a small distance. The various components of tool 100 may be cast, molded, machined, stamped, or formed from any process known to one skilled in the art. Tool 100 and its various components may be made from any material known in the art. For example, the tool may be made from stainless steel or plastic. Tool 100 may also be made from multiple materials and/or composite materials. As tool 100 may be used in a surgical setting, it may be preferable to use biocompatible materials for the construction of tool 100. Biocompatible materials may be any material that is not reactive with the body. For example, biocompatible materials may include stainless steel, polyvinylchloride, polytetraflouoroethylene, polyethersulfonate, polyethylene, polyurethane, polyetherimide, polycarbonate, polyetherketone, polysulfonate, polypropylene, and/or any other materials known in the art.

Figure 8:
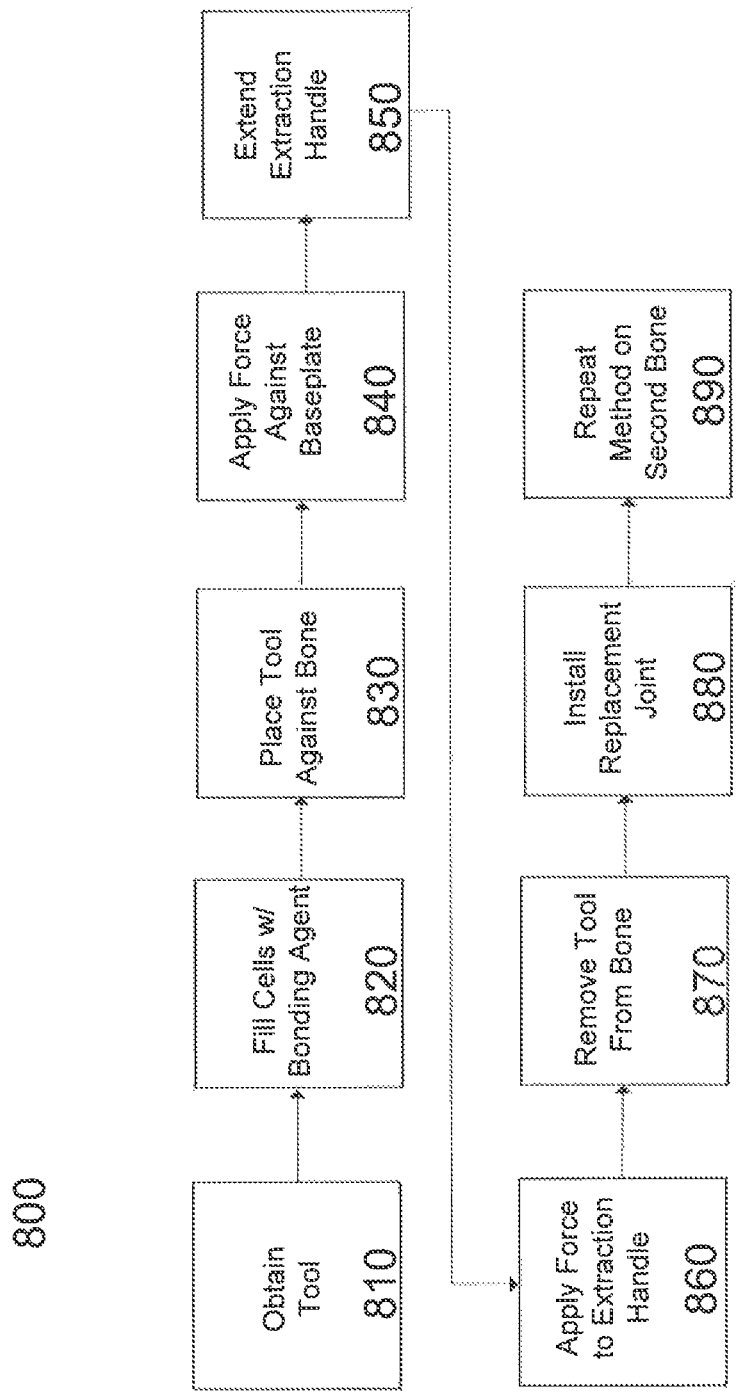
FIG. 8 is a method of using a bonding agent application tool, in accordance with various embodiments.
Figure 9:
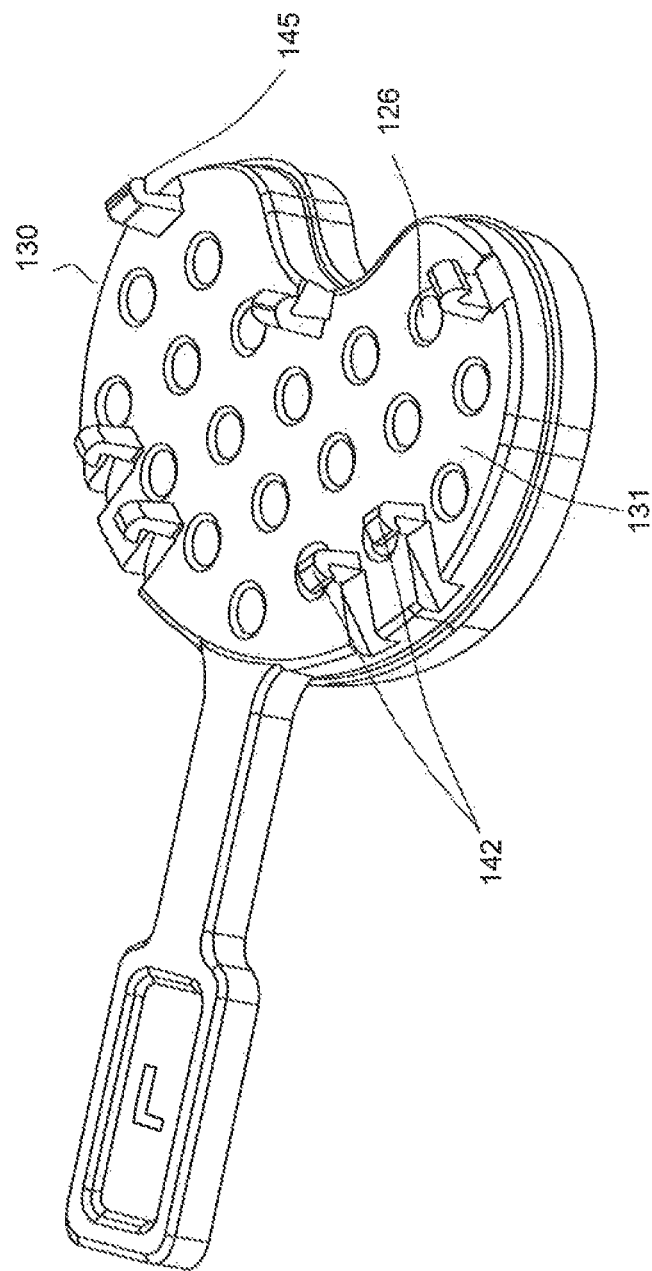
FIG. 9 is a isometric view of a top plate of a bonding agent application tool, in accordance with various embodiments.

In accordance with various embodiments, and as illustrated in FIG. 8, the present disclosure includes a method for applying a bonding agent to a bone that is prepared to receive the bonding agent as part of a joint replacement procedure. The method includes obtaining a bonding agent application tool comprising a handle and a head (step 810). The head may comprise a base plate and a plurality of cells. The cells may be filled with the bonding agent (step 820). The top of the walls of the plurality of cells may be placed against the prepared bone end where the joint is being replaced (step 830). A force may be applied to the base plate forcing the cells to cut into the bone and forcing the bonding agent into the cuts and pores in the bone (step 840). The force may be applied by striking the baseplate with a mallet. An extraction handle on the tool may be raised perpendicular to the base plate (step 850). A force may be applied to the extraction handle in the opposite direction of the bone (step 860). The tool may be removed from the end of the bone (step 870). The replacement joint may be oriented in the area prepared with the bonding agent (step 880). The method may be repeated for the second bone in the joint (step 890). In one example, the first bone may be the distal end of the femur and the second bone may be the proximal end of the tibia.

While tool 100 has been discussed herein as a tool for joint replacement surgery, tool 100 should not be limited to only this task. For example, tool 100 may be used to apply any agent or any bonding material to any surface (e.g., wood, plastic, composite materials, etc.).

Systems, methods and products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed:

1. An apparatus configured to aid in an orthopedic joint replacement comprising:
   a head having a base plate, a top plate and an external wall and a plurality of internal walls within the external wall,
   wherein the head comprises an extraction handle that has a pivot point connection between the extraction handle and the head, wherein the extraction handle is configured to rotate up and away from the base plate, and wherein the extraction handle wraps around at least half of the base plate,
   wherein the internal walls define a plurality of cells,
   wherein the plurality of cells are configured to restrict a lateral movement of a bonding agent within a first cell from flowing to a second cell,
   wherein the head is configured to be removed from a bone, while the bonding agent remains for fixating an orthopedic joint replacement; and
   the top plate comprising at least a portion of the plurality of cells and at least a portion of the external wall.

2. The apparatus of claim 1, further comprising a handle attached to the exterior side of the external wall or the base plate.

3. The apparatus of claim 1, wherein a first portion of the plurality of cells are similarly shaped and a second portion of the plurality of cells are dissimilarly shaped.

4. The apparatus of claim 1, wherein at least some of the plurality of cells are similarly shaped cells, and wherein the at least some of the plurality of cells are honeycomb shaped.

5. The apparatus of claim 1, wherein the plurality of cells include dissimilarly shaped cells that connect honeycomb shaped cells to the external wall.

6. The apparatus of claim 1, wherein the head substantially conforms to a shape of an end of the bone to which the head is applied.

7. The apparatus of claim 6, wherein the head is shaped similar to a distal end of a femur.

8. The apparatus of claim 1, further comprising a handle, wherein the longitudinal axis of the handle intersects the external wall.

9. The apparatus of claim 1, wherein the head is oblong with a convex side and a concave side and rounded on the ends.

10. The apparatus of claim 1, wherein the top plate includes pegs which are configured to align with holes in the base plate, wherein the top plate and the base plate are configured to mate allowing the top plate pegs to engage the holes in the base plate causing the base plate and top plate to be moveably attached to one another.

11. The apparatus of claim 1, wherein the top plate separates from the base plate and pegs unplug holes in the base plate.

12. The apparatus of claim 1, wherein the base plate comprises plugs, and wherein the base plate plugs align with holes defined by the plurality of cells.

13. The apparatus of claim 1, wherein at least one of the plurality of cells includes a through hole that passes through a bottom surface of the top plate defining the respective one of the cells.

14. The apparatus of claim 1, wherein at least one of the plurality of cells includes a through hole that passes through a bottom surface of the top plate defining the respective one of the cells, and wherein the through hole serves as a vent when the top plate is separated from the base plate.

15. A method for applying a bonding agent to a bone as part of a joint replacement procedure comprising:
providing a tool configured to aid in an orthopedic joint replacement, wherein the tool comprises:
a head having a base plate, a top plate and an external wall and a plurality of internal walls within the external wall,
wherein the head comprises an extraction handle that has a pivot point connection between the extraction handle and the head, wherein the extraction handle is configured to rotate up and away from the base plate, wherein the extraction handle wraps around at least half of the base plate,
wherein the internal walls define a plurality of cells,
wherein the plurality of cells are configured to restrict a lateral movement of a bonding agent within a first cell from flowing to a second cell,
wherein the head is configured to be removed from a bone, while the bonding agent remains for fixating an orthopedic joint replacement; and
the top plate comprising at least a portion of the plurality of cells and at least a portion of the external wall;
filling each of the plurality of cells with the bonding agent;
placing the top of the walls of the plurality of cells against the bone where the joint is being replaced; and
applying a force to the base plate forcing the cells to cut into the bone and forcing the bonding agent into the cuts and pores in the bone.

16. The method of claim 15, further comprising removing the tool from the bone by:
rotating the extraction handle on the tool until it is extending away from the bone and the tool;
applying a force on the extraction handle away from the bone; and
venting holes in the bottom of the plurality of cells allowing the cells to be separated from the bone.

17. An apparatus configured to aid in an orthopedic joint replacement comprising:
a head having a base plate, a top plate and an external wall and a plurality of internal walls within the external wall,
wherein the head comprises an extraction handle that has a pivot point connection between the extraction handle and the head, wherein the extraction handle is configured to rotate up and away from the base plate,
wherein the internal walls define a plurality of cells,
wherein the plurality of cells are configured to restrict a lateral movement of a bonding agent within a first cell from flowing to a second cell,
wherein at least some of the plurality of cells are similarly shaped cells,
wherein the at least some of the plurality of cells are honeycomb shaped,
wherein the head is configured to be removed from a bone, while the bonding agent remains for fixating an orthopedic joint replacement; and
the top plate comprising at least a portion of the plurality of cells and at least a portion of the external wall.

18. An apparatus configured to aid in an orthopedic joint replacement comprising:
a head having a base plate, a top plate and an external wall and a plurality of internal walls within the external wall,
wherein the head comprises an extraction handle that has a pivot point connection between the extraction handle and the head, wherein the extraction handle is configured to rotate up and away from the base plate,
wherein the internal walls define a plurality of cells,
wherein the plurality of cells are configured to restrict a lateral movement of a bonding agent within a first cell from flowing to a second cell,
wherein the plurality of cells include dissimilarly shaped cells that connect honeycomb shaped cells to the external wall,
wherein the head is configured to be removed from a bone, while the bonding agent remains for fixating an orthopedic joint replacement; and
the top plate comprising at least a portion of the plurality of cells and at least a portion of the external wall.

19. An apparatus configured to aid in an orthopedic joint replacement comprising:
a head having a base plate, a top plate and an external wall and a plurality of internal walls within the external wall,
wherein the head comprises an extraction handle that has a pivot point connection between the extraction handle and the head, wherein the extraction handle is configured to rotate up and away from the base plate,
wherein the internal walls define a plurality of cells,
wherein the plurality of cells are configured to restrict a lateral movement of a bonding agent within a first cell from flowing to a second cell,
wherein the head is configured to be removed from a bone, while the bonding agent remains for fixating an orthopedic joint replacement,
wherein the base plate comprises base plate plugs, and wherein the base plate plugs align with holes defined by the plurality of cells; and
the top plate comprising at least a portion of the plurality of cells and at least a portion of the external wall.

* * * * *